United States Patent [19]

Lamberton et al.

[11] Patent Number: 4,699,141

[45] Date of Patent: Oct. 13, 1987

[54] NEOVASCULARIZATION

[75] Inventors: Robert P. Lamberton, North Attleboro, Mass.; Milton H. Lipsky, West Greenwich, R.I.

[73] Assignee: Rhode Island Hospital, Providence, R.I.

[21] Appl. No.: 819,870

[22] Filed: Jan. 16, 1987

[51] Int. Cl.$^4$ .............................................. A61B 17/04
[52] U.S. Cl. ................................ 128/334 R; 128/1 R; 523/114
[58] Field of Search ............................ 128/344 R, 1 R; 424/14–19, 22, 28; 623/1; 523/114

[56] References Cited

U.S. PATENT DOCUMENTS

| 4,243,656 | 1/1981 | Walliczek | 424/28 |
| 4,373,217 | 2/1983 | Draenert | 523/114 |
| 4,591,496 | 5/1986 | Cohen et al. | 424/16 |
| 4,594,407 | 6/1986 | Nyilas et al. | 523/114 |

FOREIGN PATENT DOCUMENTS 2853614  7/1979  Fed. Rep. of Germany ........ 424/28

OTHER PUBLICATIONS

Gimbrone et al., "Tumor Growth and Neovascularization: An Experimental Mode Using Rabbit Cornea", in *Journal of Nat. Cancer Inst.*, vol. 52, No. 2, Feb. 1974, pp. 413–427.

Altman, "Encapsulated Human Islet Transplants in Diabetic Rats", in *Trans. Am. Soc. Artif. Intern. Organs*, 1984, vol. XXX, pp. 382–385.

*Primary Examiner*—C. Fred Rosenbaum
*Assistant Examiner*—Jerome R. Smith, Jr.

[57] ABSTRACT

Neovascularization is caused by placing a ligated blood vessel, preferably in an artery, in a sponge made of a material permitting vessel growth therein and therethrough, the material preferably being an acrylic copolymer carrying therein collagen and thereon heparin and fibrinogen, there being also in a preferred embodiment a cell receptacle with a molecular weight cutoff permeable walls within the sponge.

13 Claims, 1 Drawing Figure

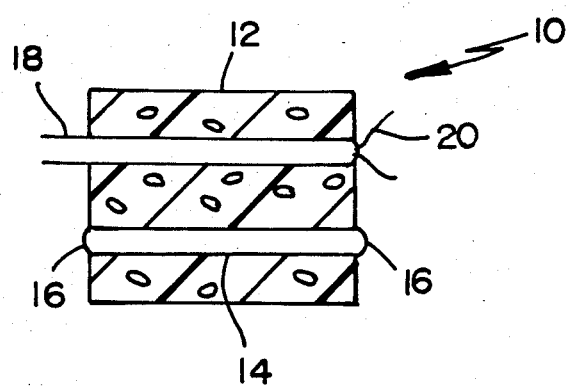

NEOVASCULARIZATION

FIELD OF THE INVENTION

This invention relates to facilitating growth of blood vessels.

BACKGROUND OF THE INVENTION

It has been known in the art that it could be desirable to implant in bodies containers of cells in permeability communication with the bodies through openings sized to prevent passage of elements that would tend to cause rejection by the bodies, "Encapsulated Human Islet Transplants in Diabetic Rats", Altman et al. (Vol. XXX Trans Am Soc Artif Intern Organs 1984).

SUMMARY OF THE INVENTION

We have discovered that neovascularization may be facilitated, both in richness of vessel denseness and the rapidity of creation of such denseness, by applying to a ligated vessel within the animal body a spongy material, as hereinafter described.

In preferred embodiments, the spongy material surrounds a permeable-wall capsule into which cells to be nourished by the neovascular grouping created as above may be introduced.

DESCRIPTION OF THE PREFERRED EMBODIMENT

The preferred embodiment, shown in the drawing, has the following structure and mode of operation.

DRAWING

The FIGURE is a view in section of the preferred embodiment of the invention.

STRUCTURE

There is generally indicated at 10 an assembly of sponge 12, diffusion chamber 14, and artery 16.

Sponge 12 is a polyurethane isocyanate sponge. Sponge 12 is prepared as follows. 75 grams of the solution of collagen (3 mg. per ml.) in 0.012N HCl sold by Collagen Corporation, Palo Alto, Calif. under the trademark VITROGEN 100 is mixed with 25 grams of distilled water, and the resultant mixture is then mixed with 50 grams of the polyurethane isocyanate acrylic copolymer ("prepolymer") sold by W. R. Grace & Co., Lexington, Mass. under the trademark Hypol 4000. This mixture foams up and within 10 minutes results in a sponge which can then be cut into pieces 12 of the desired size and shape.

Sponge 12 is then wet throughout with a solution of fibrinogen and heparin (10 ml. of a solution of heparin containing 1000 units of heparin per ml. has dissolved in it a 1 mg. package of fibrinogen available from Sigma Corporation, to provide the wetting solution).

There is then inserted through sponge 12 receptacle 14, which is a hollow polyurethane isocyanate (acrylic copolymer) fiber sold by said W. R. Grace & Co. under the trademark AMICON XM-50 and characterized by permeable walls with a nominal molecular weight cutoff of 50,000 daltons. The ends of receptacle 14 are sealed with a liquid polyurethane isocyanate material, also sold by said W. R. Grace & Co. and which acts as sort of glue with respect to the material of the receptacle, curing when wet.

Sponge 12 is shown in the drawing in situ in the animal body. Extending througuh it also is human or other animal artery 18, which has been ligated and tied off with tie 20, and then drawn through sponge 20.

OPERATION

Sponge 12 carrying empty receptacle 14 is surgically positioned in an animal body with ligated artery 18 therethrough.

Within six weeks there has grown out from artery 18, which is of course in flow contact with the animal heart an array of vessels which are then able to well nourish cells in the vicinity. Growth of these vessels, or neovascularization, is facilitated by the collagen, heparin, and fibrinogen used, and not hampered by the material of the sponge, which does not adversely affect vessel growth.

The animal is then surgically reopened, one end 20 of the receptacle opened, desired cells (e.g., pancreas cells) placed therein, and end 20 then closed again using the "glue" above disclosed.

The new array of arteries provides nourishment for the cells in the receptacle 14, and the cutoff pore size of receptacle 14 prevents the reaching of the cells in receptacle 14 of bodies that would tend to cause rejection.

OTHER EMBODIMENTS

Desired cells may be placed in receptacle 14 prior to initial surgical placing of the sponge around the artery in the body.

The vessel ligated and from which growth occurs may be a vein rather than an artery.

Vessel neovascularization may be used to support, for example, skin, bone, trachea, or tooth grafts not involving any receptacle 14.

What is claimed is:

1. A surgically implantable container for transplanted cells, comprising,
    a sponge body formed of a spongy material adapted to permit growth therein of capillary blood vessels when said sponge is placed adjacent to or surrounding a larger noncapillary blood vessel, and
    a semipermeable membrane receptacle for containing living transplanted cells mounted in said sponge body in position to communicate with blood in said growing capillary vessels, said receptacle having pores with a predetermined molecular weight cutoff size to retain cells therein and to prevent passage of bodies that would cause rejection of the cells but to permit passage of nutrients to the interior of said receptacle and the transport out of the receptacle of chemicals created therein.

2. The container of claim 1 in which said sponge body is formed of acrylic copolymer.

3. The container of claim 2 in which said receptacle is formed of acrylic copolymer hollow fiber.

4. The container of claim 1 in which said sponge body carries in said material or thereon fibrinogen, heparin, or collagen additives to facilitate said growth.

5. The method of transplanting cells which comprises placing a noncapillary blood vessel within or adjacent to a spongy material adapted to permit growth therein of capillary blood vessels, and
    providing in said spongy material a semipermeable membrane receptacle containing living transplanted cells, said receptacle being mounted in said spongy material in position to communicate with blood in said growing capillary vessels, said receptacle having pores with a predetermined molecular weight cutoff size to retain cells therein and to prevent passage of bodies that would cause rejection of the cells but to permit passage of nutrients to the interior of said receptacle and the transport out of the receptacle of chemicals created therein.

6. The method of claim 5 in which said vessel is a ligated artery.

7. The method of claim 5 in which said spongy material comprises an acrylic copolymer.

8. The method of claim 7 in which said spongy material includes therein or thereon or both fibrogen, heparin, or collagen materials tending to encourage said growth.

9. The method of claim 7 in which said one or more materials is one or more or all of collagen, heparin, and fibrinogen.

10. The container claim 2 in which said sponge body is formed of polyurethane isocyanate.

11. The container of claim 3 in which said receptacle is a polyurethane isocyanate hollow fiber.

12. The container of claim 11 in which the ends of said fiber are sealed with polyurethane isocyanate.

13. The method of claim 5 wherein said providing includes providing an empty receptacle, waiting for said capillary blood vessels to grow, and placing said cells in said receptacle.

* * * * *

UNITED STATES PATENT OFFICE
CERTIFICATE OF CORRECTION

Patent No. 4,699,141      Dated October 13, 1987

Inventor(s) Robert P. Lamberton, et al.

It is certified that error appears in the above-identified patent and that said Letters Patent are hereby corrected as shown below:

The filing date shown on the title page of the above patent should be January 16, 1986, not January 16, 1987.

Column 1, line 68, "througuh" should be --through--.

Signed and Sealed this

Seventeenth Day of May, 1988

*Attest:*

DONALD J. QUIGG

*Attesting Officer*      *Commissioner of Patents and Trademarks*